United States Patent
de Bruijn et al.

(10) Patent No.: US 6,838,284 B2
(45) Date of Patent: Jan. 4, 2005

(54) CELL CULTURE MEDIUM CONTAINING GROWTH FACTORS AND L-GLUTAMINE

(75) Inventors: Joost Dick de Bruijn, Amersfoort (NL); Gerhardus Johannes M. Tibbe, Amersfoort (NL); Sandra Claudia da Silva Madureira Mendes, Gouda (NL)

(73) Assignee: IsoTis N.V., Bilthoven (NL)

( * ) Notice: Subject to any disclaimer, the term of this patent is extended or adjusted under 35 U.S.C. 154(b) by 50 days.

(21) Appl. No.: 10/178,050

(22) Filed: Jun. 21, 2002

(65) Prior Publication Data

US 2003/0017588 A1 Jan. 23, 2003

Related U.S. Application Data

(63) Continuation of application No. PCT/NL00/00958, filed on Dec. 27, 2000.

(30) Foreign Application Priority Data

Dec. 28, 1999 (EP) .............................. 99204569

(51) Int. Cl.⁷ ................................. C12N 5/00
(52) U.S. Cl. ................ 435/404; 435/325; 435/405; 435/406; 435/408; 435/366
(58) Field of Search ................. 435/404, 405, 435/406, 408, 366, 325

(56) References Cited

U.S. PATENT DOCUMENTS

| | | | | |
|---|---|---|---|---|
| 5,733,541 A | * | 3/1998 | Taichman et al. | |
| 5,811,094 A | | 9/1998 | Caplan et al. | 424/93.7 |
| 5,830,682 A | | 11/1998 | Moore | 435/29 |
| 5,858,783 A | | 1/1999 | Goodwin et al. | 435/373 |
| 5,908,784 A | * | 6/1999 | Johnstone et al. | |
| 5,942,225 A | * | 8/1999 | Bruder et al. | |
| 6,156,570 A | * | 12/2000 | Hu et al. | |
| 6,537,782 B1 | * | 3/2003 | Shibuya et al. | |
| 6,596,274 B1 | * | 7/2003 | Abatangelo et al. | |
| 6,617,159 B1 | * | 9/2003 | Cancedda et al. | |

FOREIGN PATENT DOCUMENTS

WO    WO 98 16630    4/1998

OTHER PUBLICATIONS

ATCC Cell Lines and Hybridomas (8ᵗʰ). 1994. pp 516, 519–520 & 523.*

* cited by examiner

*Primary Examiner*—Leon B. Lankford, Jr.
(74) *Attorney, Agent, or Firm*—Banner & Witcoff, Ltd.

(57) ABSTRACT

The invention relates to a culture medium for culturing cells, in particular human cells in a process for tissue engineering bone. The medium comprises glucose, a mineral, a vitamin, a growth factor and L-glutamine, wherein the L-glutamine is present in a concentration of at least 300 mg/L.

21 Claims, 5 Drawing Sheets

CELL CULTURE MEDIUM CONTAINING GROWTH FACTORS AND L-GLUTAMINE

RELATED APPLICATIONS

This application is a continuation of prior application PCT/NL00/00958, filed on Dec. 27, 2000; which claims priority from European patent application number 99204569.0, filed Dec. 28, 1999.

FIELD OF THE INVENTION

The Invention relates to the field of tissue engineering. In particular, the invention discloses a medium and a method for culturing cells.

BACKGROUND OF THE INVENTION

The need for replacement parts for the human body, in combination with the shortage of donor tissue and/or organs has lead to the production of replacement tissue by seeding cells onto or into a scaffold. Eventually, this should lead to tissue engineered products ready to be implanted to take over the function of missing or injured body parts.

The scaffold defines the construct shape and dimensions of the replacement to be implanted. Preferably, it is manufactured of a porous or fibrous biodegradable material, so that the degradation of the scaffold proceeds parallel with accumulation of tissue components (growth and synthesis of extracellular matrix (ECM)). Thus, the function of the scaffold, the provision of shape and strength, will gradually be taken over by the formed tissue components.

In view of the fact that cells from allogenic sources are generally rejected, autologous cells isolated from a tissue biopsy from the patient to be treated are preferably used. In order to minimize the size of the biopsy needed and to minimize the time required for cell expansion, the expanded cells have to be first applied in/onto the scaffold in an efficient manner. In addition, the cells should be distributed homogeneously throughout the scaffold, in order to enable continuous neo-tissue formation.

In general, the cells that have been harvested from the patient's body are cultured in vitro for a certain period of time, either with or without a scaffold material present. During this culturing period, proliferation and/or differentiation of the cells may take place, depending on the type of cells harvested and on the objective type of tissue.

In the literature and on the market, various cell culture media are known. These usually contain glucose, inorganic salts (minerals), amino acids, and vitamins. Other ingredients that are sometimes used include ribonucleosides, deoxyribonucleosides and antibiotics. Well-known, commercially available culture media are for instance Dulbecco's Modified Minimal Eagle's Medium (DMEM) and Alpha Minimal Eagle's Medium (α-MEM).

In the U.S. Pat. No. 5,197,985, a method is disclosed for enhancing the implantation and differentiation of marrow-derived mesenchymal cells. The method is stated to be particularly intended as a means for treating skeletal and other connective tissue disorders in humans. For the culturing of the mesenchymal cells, a medium was employed that comprised the commercially available $BGJ_b$ medium (Fitton-Jackson modification) and selected lots of 10% fetal bovine serum. Further, the medium F-12 Nutrient Mixture (Ham) was used for selective marrow-derived mesenchymal cell separation.

The production of tissue engineered products will generally only commence once the type of injury or disorder is known and a specific treatment has been decided upon. While the tissue engineering is carried out, the patient is in the meantime suffering from his injuries or disorder. Thus, in order to minimize a patient's discomfort it is of great importance that the production of engineered tissues proceeds as fast as possible. A disadvantage of most of the known culture media is that they do not allow for a sufficiently fast proliferation and/or differentiation of the cells which are cultured in it. This disadvantage is particularly apparent in case human cells are cultured.

BRIEF SUMMARY OF THE INVENTION

The present invention seeks to provide a culture medium wherein cells proliferate and/or differentiate very fast. The objective of the culture medium is to allow for a reduction of the time needed for culturing cells in the treatment of a patient via a tissue engineering approach, when compared to conventional culture media.

Surprisingly, it has now been found that the rate of proliferation and/or differentiation of cells can be significantly increased by culturing them in a medium which comprises a growth factor and an increased concentration of L-glutamine. The invention accordingly relates to a culture medium comprising glucose, a mineral, a vitamin, a growth factor and L-glutamine, wherein the L-glutamine is present in a concentration of at least 300 mg/L.

DETAILED DESCRIPTION OF THE INVENTION

Figure 1:
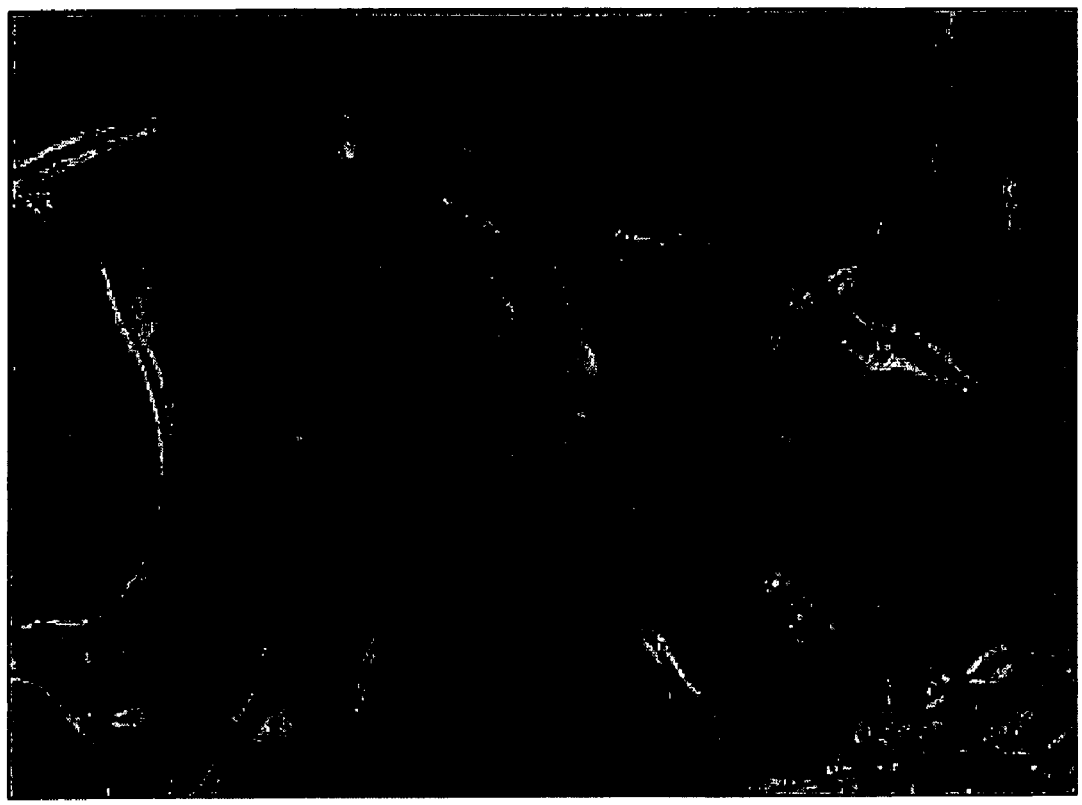
FIG. 1 depicts cells grown in medium including 10% fetal bovine serum, 0.2 mM L-ascorbic acid 2-phosphate, 0.1 mg/ml penicillin G, 50 μg/ml gentamicin and 0.3 μg/ml fungizone according to method A.

Human cells have been found to proliferate much faster in a culture medium according to the invention than in conventional culture media. Moreover, the differentiation of cells, which are capable of differentiation, has also been found to proceed faster than in conventional culture media. This increased cultivation rate is advantageous when the culture medium is employed for manufacturing a tissue engineered product for treatment of a patient.

The culture medium comprises several components, which are dissolved or suspended in a suitable liquid, preferably distilled water. As cells will be cultured in the medium, it will be clear that it is of advantage to work under sterile conditions to prevent microbial contamination of the cultures.

In order for cells to be cultivated, it is necessary that sufficient nutrients are present in the culture medium. To this end, the present culture medium comprises glucose, minerals and vitamins.

Glucose is an important nutrient in a culture medium. In accordance with the invention it is preferred that the concentration of glucose is at least 750 mg/L, more preferred between 900 and 2000 mg/L.

The minerals may suitably be chosen from the group of calcium, potassium, lithium, magnesium, sodium, sulphate, chloride, bicarbonate, dihydrogenphosphate ions, and combinations thereof. Particularly suitable minerals are calcium chloride, preferably in an amount of 100–400 mg/L, potassium chloride, preferably in an amount of 200–600 mg/L, sodium chloride, preferably in an amount of 5500–8000 mg/L, magnesium sulphate, preferably in an amount of 100–300 mg/L, sodium bicarbonate, preferably in an amount of 1500–3000 mg/L, and sodium dihydrogenphosphate, preferably in an amount of 100–200 mg/L. The concentrations of these minerals may be varied within rather wide ranges. Typically, the combined amount of minerals in a culture medium according to the invention is chosen such as to result in near physiological conditions (around 0.9%).

The vitamins may suitably be chosen from the group of L-ascorbic acid, biotin, D-calcium pantothenate, choline chloride, folic acid, i-inositol, nicotinamide, pyridoxal, riboflavin, thiamine, vitamin $B_{12}$, vitamin A (retinoic acid) and combinations thereof. These may be present in the following, preferred concentrations:

| L-ascorbic acid | 75–1500 mg/L; |
|---|---|
| biotin | 0.03–0.5 mg/L; |
| D-calcium pantothenate | 0.5–2 mg/L; |
| choline chloride | 0.5–2 mg/L; |
| folic acid | 0.5–2 mg/L; |
| i-inositol | 1–4 mg/L; |
| nicotinamide | 0.5–2 mg/L; |
| pyridoxal | 0.5–2 mg/L; |
| riboflavin | 0.03–0.5 mg/L; |
| thiamine | 0.05–2 mg/L; and |
| vitamin $B_{12}$ | 1–2 mg/L. |

It is further preferred that the present culture medium comprises amino acids. Suitably, these amino acids are selected from the following group in the specified concentrations:

| L-alanine | 10–50 mg/L; |
|---|---|
| L-arginine | 75–150 mg/L; |
| L-asparagine | 30–80 mg/L; |
| L-aspartic acid | 10–50 mg/L; |
| L-cystine | 10–50 mg/L; |
| L-cysteine | 75–130 mg/L; |
| L-glutamic acid | 50–100 mg/L; |
| L-alanyl-L-glutamine | 5–20 mg/L |
| glycine | 30–80 mg/L; |
| L-histidine | 20–60 mg/L; |
| L-isoleucine | 30–80 mg/L; |
| L-leucine | 30–80 mg/L; |
| L-lysine | 50–100 mg/L; |
| L-methionine | 5–30 mg/L; |
| L-phenylalanine | 10–50 mg/L; |
| L-proline | 20–60 mg/L; |
| L-serine | 10–50 mg/L; |
| L-threonine | 30–80 mg/L; |
| L-tryptophan | 5–15 mg/L; |
| L-tyrosine | 10–60 mg/L; and |
| L-valine | 30–80 mg/L. |

The combined concentration of the amino acids preferably lies between 800 and 5000 mg/L. It is to be noted that this concentration range does not include L-glutamine.

L-glutamine is an important component of a culture medium according to the invention. It has been found that a concentration L-glutamine of at least 300 mg/L, preferably between 400 and 800 mg/L leads to a particular high proliferation and/or differentiation rate of cells cultured in the present culture medium.

Another component of a culture medium according to the invention is a growth factor. The nature of the growth factor may suitably be chosen dependent on the type of cells to be cultured. Examples of preferred growth factors are Bone Morphogenetic Protein (BMP), Epidermal Growth Factor (EGF), basic Fibroblast Growth Factor (bFGF), Nerve Growth Factor (NGF), Bone Derived Growth Factor (BDGF), Transforming Growth Factor-β1 (TGF-β1), and human Growth Hormone (hGH). In a preferred embodiment, the culture medium is employed to culture cells which are used in tissue engineering bone. In accordance with this embodiment, the growth factor is preferably bFGF. The growth factor is preferably present in an amount between 0.1 µg/L and 10 µg/L.

In a preferred embodiment, the present culture medium further comprises an antibiotic or a combination of antibiotics. Examples of suitable antibiotics include penicillin G, gentamicin, fungizone, streptomycin. It has surprisingly been found that the nature of the antibiotic influences that cultivation rate of cells in the present culture medium. A highly preferred combination of antibiotics is penicillin G and streptomycin. These antibiotics are preferably each employed in an amount of 50–150 µg/mL, more preferably they are both employed in an amount of 100 µg/mL. The total amount of antibiotics in a culture medium according to the invention preferably lies between 75 and 300 µg/mL.

The culture medium may further comprise any ingredient conventionally employed in culture media. Examples of such ingredients include serum, such as fetal bovine serum, autologous serum or synthetic serum (e.g. Ultrocer®), thioctic acid, phenol red, sodium pyruvate, ribonucleosides and deoxyribonucleosides. A ribonucleoside or a deoxyribonucleoside is preferably present in a concentration of between 5 and 15 mg/L. It is to be noted that when serum is used, it is added after the formulation of the culture medium. In other words, the amount of serum added dilutes the concentrations mentioned herein. Fetal bovine serum may be added in such an amount that the composition of serum and culture medium comprises between 5 and 15 vol. % of serum. Ultrocer® may be added in such an amount that the composition of serum and culture medium comprises between 1 and 10 vol. % of serum.

As has been mentioned above, the present culture medium is particularly useful for culturing human cells, e.g. in a process for manufacturing tissue engineered products, such as skin grafts, bone implants, cartilage implants. The present culture medium has particularly been found advantageous for the in vitro production of bone tissue. More osteogenic cells are formed resulting in a higher success of bone formation after implantation, when the cells are cultured in a culture medium in accordance with the invention when compared to conventional culture media.

In principle, cells of any type may be cultivated in a culture medium according to the invention. Preferred cell types include stem cells, progenitor cells, mesenchymal cells, epithelial cells, cartilaginous cells, osseous cells, muscular cells, gland cells, fat cells, pericytes, satellite cells and dermal cells. Highly preferred cells to be cultured in the present culture medium are progenitor cells which may differentiate into bone. Differentiation of the cells may be facilitated by the presence of growth factors, such as Bone Morphogenetic Protein, or dexamethasone, which is preferably used in an amount of between $1*10^{-9}$ and $1*10^{-7}$ μg/L. The cells may be cultured in the presence of a scaffold or without a scaffold. If the cells are cultured in the presence of a scaffold, they can first suitably be seeded onto or into the scaffold in any known manner.

The invention will now be elucidated by the following, non-restrictive examples.

EXAMPLE I

A culture medium was prepared by admixing the following ingredients in the specified concentrations in water:

| Component | 1 × Liquid mg/L |
|---|---|
| INORGANIC SALTS | |
| $CaCl_2.2H_2O$ | 264.00 |
| KCl | 400.00 |
| $MgSO_4.7H_2O$ | 200.00 |
| NaCl | 6800.00 |
| $NaHCO_3$ | 2200.00 |
| $NaH_2PO_4.2H_2O$ | 158.00 |
| OTHER COMPONENTS | |
| D-Glucose | 1000.00 |
| DL-68 Thioctic Acid | 0.20 |
| Phenol Red | 10.00 |
| Sodium Pyruvate | 110.00 |
| AMINO ACIDS | |
| L-Alanine | 25.00 |
| L-Arginine.HCl | 127.00 |
| L-Asparagine.$H_2O$ | 50.00 |
| L-Aspartic Acid | 30.00 |
| L-Cystine | 24.00 |
| L-Cysteine HCl | 100.00 |
| L-Glutamic Acid | 75.00 |
| Glycine | 50.00 |
| L-Histidine HCl.$H_2O$ | 42.00 |
| L-Isoleucine | 53.00 |
| L-Leucine | 52.00 |
| L-Lysine.HCl | 73.00 |
| L-Methionine | 15.00 |
| L-Phenylalanine | 32.00 |
| L-Proline | 40.00 |
| L-Serine | 25.00 |
| L-Threonine | 48.00 |
| L-Tryptophan | 10.00 |
| L-Tyrosine | 36.00 |
| L-Valine | 46.00 |
| VITAMINS | |
| L-Ascorbic Acid | 50.00 |
| Biotin | 0.10 |
| D-Ca Pantothenate | 1.00 |
| Choline Chloride | 1.00 |
| Folic Acid | 1.00 |
| 1-Inositol | 2.00 |
| Nicotinamide | 1.00 |
| Pyridoxal HCl | 1.00 |
| Riboflavin | 0.10 |
| Thiamine HCl | 1.00 |
| Vitamin $B_{12}$ | 1.40 |
| RIBONUCLEOSIDES | |
| Adenosine | 10.00 |
| Cytidine | 10.00 |
| Guanosine | 10.00 |
| Uridine | 10.00 |
| DEOXYRIBONUCLEOSIDES | |
| 2'Deoxyadenosine | 10.00 |
| 2'Deoxycytidine HCl | 11.00 |
| 2'Deoxyguanosine | 10.00 |
| 2'Deoxythymidine | 10.00 |
| penicillin G | 100 μg/mL |
| streptomycin | 100 μg/mL |
| bFGF | 1 ng/mL |
| L-glutamine | 584 mg/L |

EXAMPLE II

Introduction.

In order to culture Human Bone Marrow Cells (HBMC's) efficiently it is necessary to develop a suitable cell culture medium. We compared two different media to investigate which type is most suitable for culturing HBMC's and to see if there is a difference in, in vivo, bone formation after culturing these cells on a CaP scaffold. We performed several studies on HBMC's obtained of several different patients using either α-MEM containing 10% Fetal Bovine Serum (FBS), 0.2 mM L-ascorbic acid 2-phosphate (AsAP), 0.1 mg/ml penicillin G, 50 μg/ml gentamicin and 0.3 μg/ml fungizone (AB) or in α-MEM containing 10% FBS, 0.2 mM L-ascorbic acid 2-phosphate (AsAP), 1 ng/ml basic Fibroblast Growth Factor (bFGF), 2 mM L-glutamine (L-Glu), 100 U/ml penicillin, 100 μg/ml streptomycin (pen/strep) and 1% (50 U/ml) heparin (added in primary cultures only) and compared morphology, growth rates and bone formation. It was found that the combination of L-ascorbic acid, heparin, bFGF, L-Glutamine and penicillin/streptomycin in our culture medium enhanced cell-growth and showed a higher extent of bone formation.

Materials and Methods.

Human Bone Marrow Cell Collection and Culture

Method A

Bone marrow aspirate was obtained from the iliac crest of a patient. In short 5 ml of aspirate was resuspended in 20 ml α-MEM containing 50 U/ml heparin and 10% fetal bovine serum. The cell suspension is then resuspended using a 20G needle and centrifuged for 10 minutes at 300 g. The supernatant is discarded and the cell pellet is resuspended in α-MEM containing 10% FBS, 0.2 mM L-ascorbic acid 2-phosphate (AsAP), 0.0 mg/ml penicillin G, 50 μg/ml gentamicin and 0.3 μg/ml fungizone (AB). The obtained mononucleated cells are then plated at a density of ±500.000 cells/$cm^2$ in tissue culture flasks. Cells were grown at 37° C. with 5% $CO_2$ in a humid atmosphere. The culture medium is refreshed twice a week and at near confluency the adherent cells are washed with phosphate buffered saline solution (PBS) and enzymatically released by incubating the cells with a 0.25% Trypsin-EDTA solution at 37° C. for at least 10 Minutes. The released cells are then thoroughly resuspended and replated at a density of 5000–10.000 cells/$cm^2$ subsequent passages (up to the fifth passage) are performed when cells reach near confluency and cell morphology is monitored with light microscopy.

Method B

Bone marrow aspirate was obtained from the iliac crest of a patient. In short 5 ml of aspirate was resuspended in 20 ml α-MEM containing 50 U/ml heparin and 10% fetal bovine serum. The cell suspension is then resuspended using a 20G needle and centrifuged for 10 minutes at 300 g. The supernatant is discarded and the cell pellet is resuspended in α-MEM containing 10% FBS, 0.2 mM AsAP, 1 ng/ml bFGF, 2 mM L-glutamine (L-Glu), 100 U/ml penicillin and 100 μg/ml streptomycin (pen/strep) and 1% (50 U/ml) heparin (added in primary cultures only). The obtained mononucleated cells are then plated at a density of ±500.000 cells/$cm^2$ in tissue culture flasks. Cells were grown at 37° C. with 5% $CO_2$ in a humid atmosphere. The culture medium is refreshed twice a week and at near confluency the adherent cells are washed with phosphate buffered saline solution (PBS) and enzymatically released by incubating the cells with a 0.25% Trypsin-EDTA solution at 37° C. for at least 10 Minutes. The released cells are then thoroughly resuspended and replated at a density of 5000–10.000 cells/cm² subsequent passages (up to the fifth passage) are performed when cells reach near confluency and cell morphology is monitored with light microscopy.

In Vivo Experiments and Histology.

Porous CaP particles of size 2 by 3 mm are used for culturing the released HBMC's on. In short harvested HBMC's of several passages were seeded in a density of 100.000–200.000 cells/particle. The cells were cultured during one week using α-MEM containing 10% FBS, 0.2 mM ASAP, 10 nM Dexamethason (Dex) and 10 mM beta glycerophosphate (βGP) before implantation.

Shortly before implantation the samples were soaked in α-MEM, washed in PBS and subcutaneously implanted into nude mice and kept in vivo for 4–6 weeks. Control samples incubated in both media, without cells were also implanted.

At the end of the in vivo period the implanted samples were removed and immediately fixated in 1.5% glutaraldehyde in 0.14 M cacodylic acid buffer, pH 7.2–7.4.

After dehydration in an alcohol series and embedding in methyl methacrylate, the samples are sectioned on a Histological diamond innerlock saw (Leyden Microtome cutting system). Sections of around 10 μm are stained with basic fuchsin and methylene blue, in order to study bone formation. The sections were then scored per patient for bone formation.

Results.

Morphology.

Medium with AB (Method A): FIG. 1 shows that often larger, flatter cell morphology observed. Cell growth was limited, and there was only occasionally bone formation observed after subcutaneous implantation.

Figure 2:
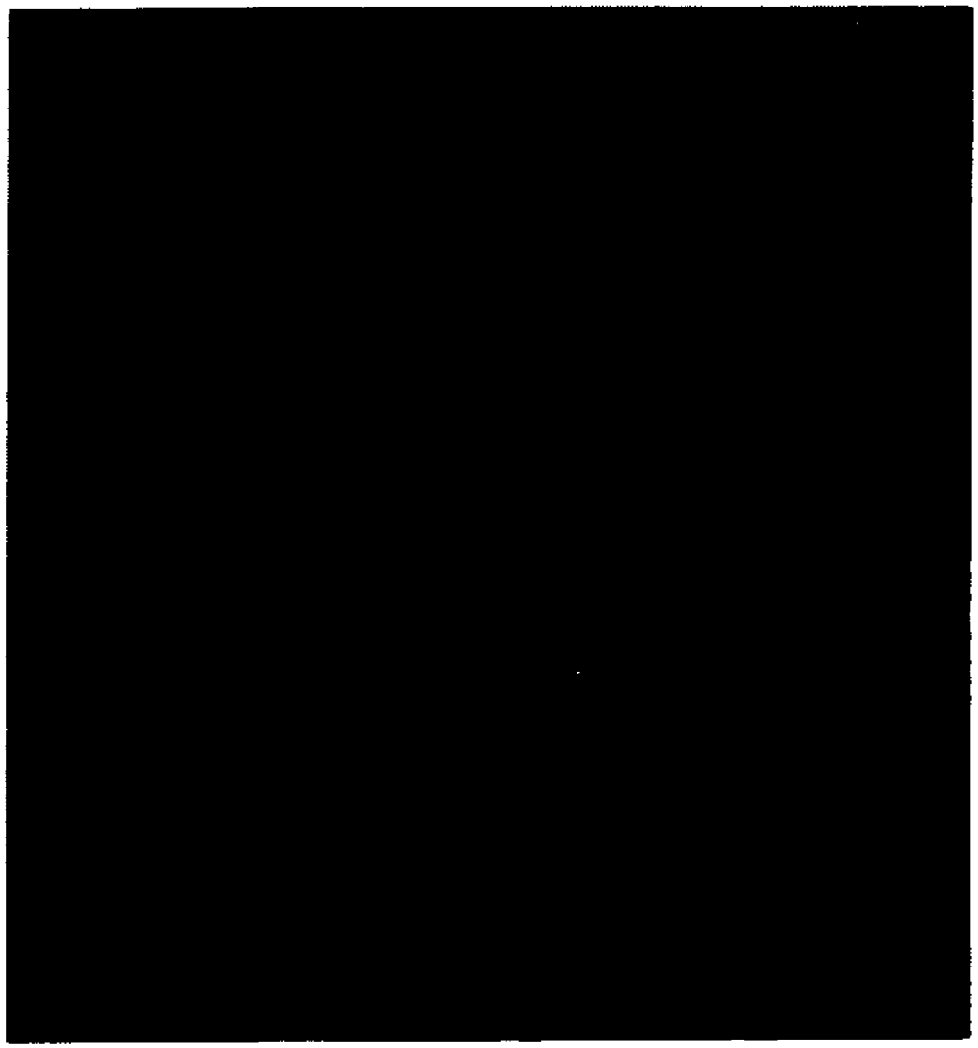
FIG. 2 depicts cells grown in improved medium according to method B.
Figure 3:
FIG. 3 depicts de novo bone formation after subcutaneous implantation.

Improved medium (Method B): FIG. 2 shows that cells with spindle shaped and fibroblastic morphology were obtained. Rapid cell proliferation was observed. Also, De Novo bone formation after subcutaneous implantation was widespread (see FIG. 3).

Figure 4:
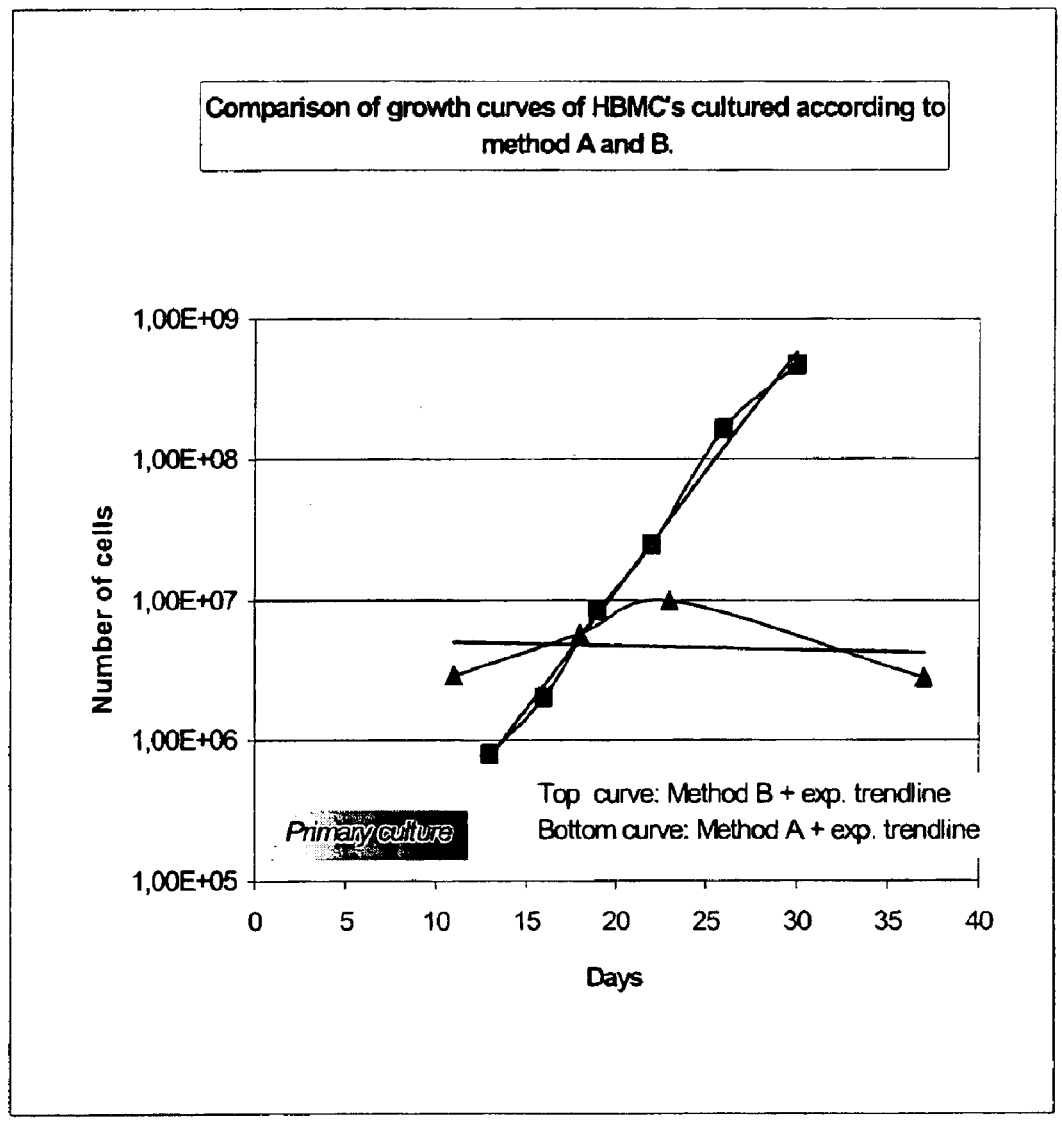
FIG. 4 graphically depicts growth curves of cells cultured using methods A and B.

FIG. 4 shows a comparison of the growth curves of the cells cultured with methods A and B.

Figure 5:
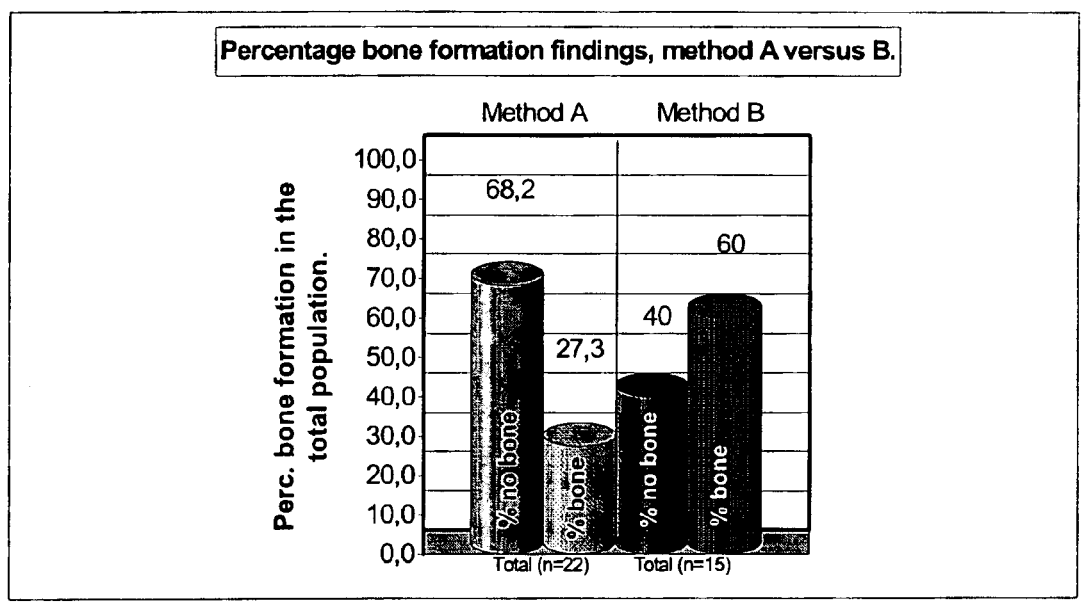
FIG. 5 graphically depicts bone formation in 22 patients using cells cultured by method A and in 15 patients using cells cultured by method B.

FIG. 5 shows a comparison of 22 patients cultured with method A and 15 patients cultured with method B, in relation to bone formation.

Discussion.

HBMC's cultured according to method B showed a linear culture expansion compared to HBMC's cultured according to method A. The growth rate of the two methods observed show that culturing HBMC's according to method B, results in a higher growth rate than observed for method A. In time culturing HBMC's with α-MEM containing 10% FBS, 0.2 mM AsAP, 0.1 mg/ml penicillin G, 50 μg/ml gentamicin and 0.3 μg/ml fungizone (method A) shows a decrease in cell growth. Use of culture medium comprising of bFGF, L-Glu, pen/strep, AsAP, with the addition of 50 U/ml heparin in primary cultures has shown an improved morphology, growth rate and in vivo osteogenic character of the cells, after they have been stimulated to osteoprogenitor differentiation with dexamethasone.

What is claimed is:

1. Culture medium comprising glucose, a mineral, a vitamin, a growth factor and L-glutamine, wherein the L-glutamine is present in a concentration of at least 300 mg/L and wherein the vitamin is L-ascorbic acid in an amount between 75 and 1500 mg/L.

2. Culture medium according to claim 1, wherein the L-glutamine is present in a concentration between 400 and 800 mg/L.

3. Culture medium according to claim wherein L-ascorbic acid is added in the form of L-ascorbic acid-2-phosphate.

4. Culture medium according to claim 1, wherein the growth factor is chosen from the group of bone morphogenetic protein, epidermal growth factor, basic fibroblast growth factor, nerve growth factor, bone derived growth factor, transforming growth factor-β1, and human growth hormone.

5. Culture medium according to claim 4, wherein the factor is basic fibroblast growth factor.

6. Culture medium according to claim 5, wherein the basic fibroblast growth factor is present in a concentration between 0.1 and 10 μg/L.

7. Culture medium according to claim 1, wherein the mineral comprises one or more ions chosen from the group of calcium, potassium, lithium, magnesium, sodium, sulfate, chloride, bicarbonate, and dihydrogenphosphate ions.

8. Culture medium according to claim 7, wherein the mineral is present in a concentration between 5 and 15 g/L.

9. Culture medium according to claim 1, further comprising a vitamin chosen from the group consisting of biotin, D-calcium pantothenate, choline chloride, folic acid, i-inositol, nicotinamide, pyridoxal, riboflavin, thiamine vitamin $B_{12}$, vitamin A and combinations thereof.

10. Culture medium according to claim 1 comprising one or more amino acids chosen from the group of L-alanine, L-arginine, L-asparagine, L-aspartic acid, L-cysteine, L-cysteine, L-glutamic acid, L-alanyl-L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

11. Culture medium according to claim 10, wherein the amino acids are present in a concentration between 0.8 and 5 g/L.

12. Culture medium according to claim 1, comprising an antibiotic.

13. Culture medium according to claim 12, wherein the antibiotic is chosen from the group of penicillin G, gentamicin, fungizone, and streptomycin.

14. Culture medium according to claim 13 comprising as antibiotic a combination of penicillin G and streptomycin, wherein both penicillin G and streptomycin are present in an amount of 50–150 μg/mL.

15. Culture medium according to claim 1 comprising dexamethasone.

16. Culture medium according to claim 1 comprising distilled water.

17. Culture medium according to claim 1 comprising a ribonucleoside and/or a deoxyribonucleoside.

18. Culture medium according to claim 1 further comprising serum.

19. Use of a culture medium according to claim 1 for culturing human cells, comprising the steps of:

obtaining human cells; and culturing the human cells in the culture medium of claim 1.

20. Use according to claim 19, wherein the cells are chosen from the group of stem cells, progenitor cells, mesenchymal cells, epithelial cells, cartilaginous cells, osseous cells, muscular cells, gland cells, fat cells, pericytes, satellite cells and dermal cells.

21. Use according to claim 20, wherein the cells are progenitor cells.

* * * * *